United States Patent [19]

Jaworski

[11] B 3,981,718

[45] Sept. 21, 1976

[54] METHOD FOR INCREASING THE SUCROSE CONTENT OF GROWING PLANTS

[75] Inventor: Ernest G. Jaworski, Olivette, Mo.

[73] Assignee: Monsanto Company, St. Louis, Mo.

[22] Filed: Dec. 20, 1974

[21] Appl. No.: 535,076

[44] Published under the second Trial Voluntary Protest Program on January 20, 1976 as document No. B 535,076.

[52] U.S. Cl. .................................................. 71/113
[51] Int. Cl.² .......................................... A01N 9/24
[58] Field of Search ................................. 71/76, 113

[56] References Cited

UNITED STATES PATENTS

| | | | |
|---|---|---|---|
| 3,282,987 | 11/1966 | Ellis | 71/113 |
| 3,712,804 | 1/1973 | Muller et al. | 71/113 |
| 3,853,530 | 12/1974 | Franz | 71/76 |

*Primary Examiner*—Glennon H. Hollrah
*Attorney, Agent, or Firm*—Arnold H. Cole; Donald W. Peterson

[57] ABSTRACT

The sucrose content of sugar cane plants is increased by treating the plants, prior to harvest, with N-methylated glycines and certain salts thereof.

7 Claims, No Drawings

METHOD FOR INCREASING THE SUCROSE CONTENT OF GROWING PLANTS

This invention relates to a method for increasing the sucrose content of growing plants. More particularly, this invention is concerned with a method wherein sugar cane plants are subjected to a chemical treatment which serves to increase the amount of harvestable sucrose in said plants.

It is known that certain derivatives of various amino acids have been used to regulate the growth of desirable crop plants. For example, U.S. Pat. No. 2,734,816 describes the use of amino acids which have been acylated with a nuclearly chlorinated phenoxyacetic acid to increase fruit set and fruit size. In specific connection with enhancing the yield of sucrose from sugar cane plants, U.S. Pat. No. 3,556,762 teaches the use of amino acid derivatives of aminoalkylenephosphonic acids, such compounds requiring the presence of three acid groups on the central nitrogen atom. Similarly, the use of derivatives of N-phosphonomethylglycine for treatment of sugar cane is disclosed in U.S. Pat. No. 3,853,530, these compounds requiring the presence of two acid groups on the central nitrogen atom.

It has now been found that N-methylated glycines and certain salts thereof, when applied to sugar producing plants in the manner hereinafter described, serve to increase the amount of recoverable sucrose in such plants. It is believed that this desirable effect results from an action of the chemical to reduce or retard further vegetative growth of the treated plant just prior to its harvest. Thus, the reducing sugars which are stored in the plant are not used as energy for plant growth but are rather converted to recoverable sucrose.

The active ingredients employed in practicing the method of this invention are illustrated by the formula

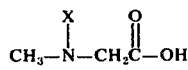

wherein X represents hydrogen or methyl. As is well understood in the art, such active ingredients can be applied in their acid form, or, if desired, said acids can be applied as non-phytotoxic, agriculturally acceptable salts such as hydrochloride, alkali metal, amine or ammonia salts.

In determining the appropriate rates and times of application to sugar cane plants, it is necessary to consider both the chronological age of the plant and its stage of maturity since cane, depending upon the practice in different geographical areas, is grown from 9 to about 30 months before harvest. Application at a rate of from about 0.11 to 5.6 kg. per hectare can be made from about 2 to 8 weeks prior to the projected harvest date. Preferably, such applications are made from 3 to 7 weeks before said date.

The active ingredients of this invention can be conveniently applied to the plants as an aqueous solution or suspension. The active ingredient can, of course, be in its free acid form although it may be employed in the form of any of the above defined salts in order to improve such ancillary features as solubility or stability. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface active agents which are convenient to use in liquid compositions of this invention are of the non-ionic type such as alkyl phenoxy poly (ethyleneoxy) ethanols, polyethylene oxide adducts of fatty and resin acids, and long chain alkyl mercaptan adducts with ethylene oxide.

A particularly preferred carrier for the acids or salts of this invention is water with about 0.1 to 2.0 percent by weight of surfactant added thereto. Alternatively, the aqueous carrier can be replaced by a non-toxic mineral oil as such, or as an oil-in-water or water-in-oil emulsion. It has been found convenient to apply the compositions to the plants in the form of aqueous solutions, suspensions or emulsions, the dilution being such that a spray volume of from about 10 to 30 liters of liquid per hectare will contain the desired dosage of active ingredient. It will be recognized, however, that higher or lower total spray volumes can be beneficially employed depending upon the particular dispensing apparatus and other factors well understood by those skilled in the art.

The specific examples which follow are presented as illustrative, non-limiting demonstrations of the useful and unexpected properties of the acids and salts of this invention.

EXAMPLE I 0.5 Gram of sarcosine (in the form of the HCl salt) is dissolved in 4 ml. water that contains as a surfactant about 0.25 percent (w./w.) nonylphenol which was ethoxylated to contain about 10.5 mols. of ethylene oxide per mol. of nonylphenol ("Tergitol NPX"). 0.6 ml. of this solution is deposited or dropped by means of a syringe with a fine needle on the spindle area at the top of the last visible dewlap of each of 20 stalks of sugar cane. (A dewlap is the junction between the blade of the leaf and the sheath which clasps the stalk). Ten of these stalks were harvested 4 weeks after such treatment and 10 more were harvested 5 weeks after such treatment.

The top 15 joints of the treated cane as well as those of similar untreated cane are removed, combined and analyzed in terms of juice purity and pol percent cane, following the so-called "press method" developed by T. Tanimoto, Hawaiian Planters Record, 57, 133 (1964). "Pol percent cane" is a polarmetric determination and equals the percentage of sucrose if the latter is the only substance in the solution which will rotate the plane of polarized light. In any event, determination of the pol percent cane is a standard and effective method for determining the sucrose content of sugar cane. The results are given below:

|  | FOUR WEEKS | | FIVE WEEKS | |
| --- | --- | --- | --- | --- |
|  | Juice Purity | Pol% Cane | Juice Purity | Pol% Cane |
| Control (untreated) | 75.00 | 9.90 | 80.00 | 11.57 |
| Treated | 82.48 | 12.49 | 81.78 | 11.82 |

These results clearly show an improvement in both sucrose yield and juice purity of the treated plants.

EXAMPLE II

The procedures described in the preceding example are repeated with N,N-dimethylglycine (in the form of the HCl salt) on another variety of sugar cane plants about 4 months later with the following results:

|  | FOUR WEEKS | | FIVE WEEKS | |
|---|---|---|---|---|
|  | Juice Purity | Pol% Cane | Juice Purity | Pol% Cane |
| (Control (untreated) | 64.24 | 6.57 | 67.32 | 7.19 |
| Treated | 68.79 | 7.28 | 64.00 | 6.21 |

The treated plants again clearly demonstrate a substantial gain in both of the factors measured at the early harvest, while a decrease in these factors occurs at the later harvest.

EXAMPLE III

The procedures described in the preceding examples are repeated about 7 months after the second testing using the compound of Example I with the following results:

|  | FOUR WEEKS | | FIVE WEEKS | |
|---|---|---|---|---|
|  | Juice Purity | Pol% Cane | Juice Purity | Pol% Cane |
| Control (untreated) | 71.22 | 7.27 | 70.94 | 8.04 |
| Treated: | 63.93 | 6.33 | 75.36 | 9.30 |

Desirable improvements of each measured factor are noted at the later harvest, while a decrease in these factors occurs at the earlier harvest.

Although the invention has been described herein with respect to specific embodiments, the details thereof are not to be construed as limitations except to the extent defined in the following claims.

What is claimed is:

1. A method for increasing the sucrose content of sugar cane plants which comprises applying to said plants, from about 2 to 8 weeks prior to harvest, an effective amount of a compound of the formula

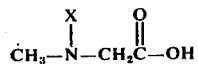

wherein X represents hydrogen or methyl, and the non-phytotoxic, agriculturally acceptable salts thereof.

2. A method as defined in claim 1 wherein said compound is an acid.

3. A method as defined in claim 2 wherein X is hydrogen.

4. A method as defined in claim 2 wherein X is methyl.

5. A method as defined in claim 1 wherein application is at a rate of about 0.11 to 5.6 kg. per hectare.

6. A method as defined in claim 1 wherein application is made from about 3 to 7 weeks prior to harvest.

7. A method as defined in claim 2 wherein application is made from about 3 to 7 weeks prior to harvest.

* * * * *